US00PP18256P2

(12) United States Plant Patent
Eggleton

(10) Patent No.: US PP18,256 P2
(45) Date of Patent: Nov. 27, 2007

(54) ***LAVANDULA* PLANT NAMED 'BOYSENBERRY RUFFLES'**

(50) Latin Name: *Lavandula stoechas*
Varietal Denomination: Boysenberry Ruffles

(76) Inventor: Steven Eggleton, 3 Harris Rd, Wonga Park, Melbourne Vic (AU), 3115

( * ) Notice: Subject to any disclaimer, the term of this patent is extended or adjusted under 35 U.S.C. 154(b) by 24 days.

(21) Appl. No.: 11/435,487

(22) Filed: May 16, 2006

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV ROM GTITM Computer Database 2006/04 Citation for Boysenberry Ruffles.*

* cited by examiner

*Primary Examiner*—Wendy C. Haas

(57) ABSTRACT

A new cultivar of *Lavandula* plant named 'BOYSENBERRY RUFFLES' that is characterized by early and repeat flowering, dense plant habit, short peduncle length, and fragrant purple flower spikes with medium light-pink sterile bracts. In combination these traits set 'BOYSENBERRY RUFFLES' apart from all other existing varieties of *Lavandula* known to the inventor.

2 Drawing Sheets

Genus: *Lavandula*. Species: *stoechas*.
Denomination: 'BOYSENBERRY RUFFLES'.

BACKGROUND OF THE INVENTION

The present invention relates to a new and distinct cultivar of lavender known botanically as *Lavandula stoechas* and hereinafter referred to by the cultivar name 'BOYSENBERRY RUFFLES'.

The new *Lavandula* cultivar named 'BOYSENBERRY RUFFLES' is one individual selection in the Australian lavender 'Ruffles Series', that resulted from a formal breeding program. The breeding program was established in November 2001 and conducted by the inventor's nursery in Victoria, Australia. The inventor, a specialists in the genus *Lavandula,* selected 'BOYSENBERRY RUFFLES' in 2003. Selection was based on a combination of repeat flowering, dense plant habit, light-pink sterile bracts that are of medium length, and short peduncle length.

'BOYSENBERRY RUFFLES' is a selection arising from the controlled cross-pollination of *Lavandula stoechas* 'Kew Red' (unpatented) as the female parent, and *Lavandula stoechas* 'Pukehou' (unpatented) as the male parent. Cross-pollination of the parent plants took place in Park Orchards, Victoria, Australia in November 2001. From this cross the F1 generation was raised in February 2002 and grown to flowering maturity in September 2002. At this stage the F1 generation was self-pollinated and the seed sown in February 2003. From these F2 seedlings a selection was made when the plants had grown to flowering stage in 140 mm. containers.

'BOYSENBERRY RUFFLES' is a perennial suitable for use in container and in the landscape. Cultural requirements include full sun, adequate but not excess water, and well-draining soil. Mature height is 60 cm. and mature width is 70 cm. 'BOYSENBERRY RUFFLES' exhibits early and repeat flowering, dense plant habit, scented grey-green foliage, short peduncle length, and scented flower spikes with light-pink sterile bracts of medium length. The traits that distinguish 'BOYSENBERRY RUFFLES' from the female parent 'Kew Red' are sterile bract length, sterile bract color, and plant habit. 'Kew Red' exhibits short sterile bract length, mid-pink sterile bract color, and is very dense in habit, whereas 'BOYSENBERRY RUFFLES' exhibits longer medium sterile bracts of a lighter pink color, and less dense plant H. The traits that distinguish 'BOYSENBERRY RUFFLES' from the male parent 'Pukehou' are peduncle length, plant habit, and sterile bract color. 'Pukehou' exhibits a long peduncle length, medium to sparse plant habit, and purple sterile bract color, compared to 'BOYSENBERRY RUFFLES' that exhibits a short peduncle length, dense plant habit, and sterile bracts that are lightpink in color.

The new *Lavandula* cultivar, named 'BOYSENBERRY RUFFLES' was first asexually propagated by the inventor in 2004. Asexual propagation was accomplished at the inventor's nursery in Australia, and the method utilized was tip cuttings. Since that time 'BOYSENBERRY RUFFLES' has been determined stable, and reproduces true to type in successive generations of asexual propagation.

SUMMARY OF THE INVENTION

The following traits have been repeatedly observed and represent the distinguishing characteristics of the new *Lavandula* cultivar named 'BOYSENBERRY RUFFLES'. These traits in combination distinguish 'BOYSENBERRY RUFFLES' from all other existing varieties of *Lavandula* known to the inventor. 'BOYSENBERRY RUFFLES' has not been tested under all possible conditions and phenotype differences may be observed with variations in environmental, climatic, and cultural conditions, without however, any variance in genotype.

1. 'BOYSENBERRY RUFFLES' exhibits dense plant habit.
2. 'BOYSENBERRY RUFFLES' exhibits second purple flower spikes and medium length sterile bracts that are light-pink in color.

3. 'BOYSENBERRY RUFFLES' exhibits repeat flowering.
4. 'BOYSENBERRY RUFFLES' exhibits fragrant grey-green foliage.
5. 'BOYSENBERRY RUFFLES' is one selection in the Australian lavender 'Ruffles Series' that blooms an average of two weeks earlier than many lavenders in commerce.
6. 'Cultural requirements for 'BOYSENBERRY RUFFLES' are full sun, adequate but not excess water and well-draining soil.
7. 'BOYSENBERRY RUFFLES' exhibits short peduncle length.
8. 'BOYSENBERRY RUFFLES' is 60 cm in height and 70 cm. in width at maturity.
9. BOYSENBERRY RUFFLES' is asexually propagated utilizing the method of tip and stem cuttings.
10. 'BOYSENBERRY RUFFLES' is suitable for use as an ornamental plant in container or in the landscape.
11. 'BOYSENBERRY RUFFLES' is hardy to USDA Zone 8.

BRIEF DESCRIPTION OF THE DRAWINGS

The accompanying drawings illustrate the overall appearance of the new *Lavandula* cultivar named 'BOYSENBERRY RUFFLES' showing the colors as true as it is reasonably possible to obtain in color reproductions of this type. Color in the drawings may differ from the color values cited in the detailed botanical description, which accurately describe the actual color of the new *Lavandula* variety named 'BOYSENBERRY RUFFLES'. The drawings were made of 9-month-old plants greenhouse grown in 16 cm containers.

The drawing labeled

The drawing labeled

BOTANICAL DESCRIPTION OF THE PLANT

Figure 1:
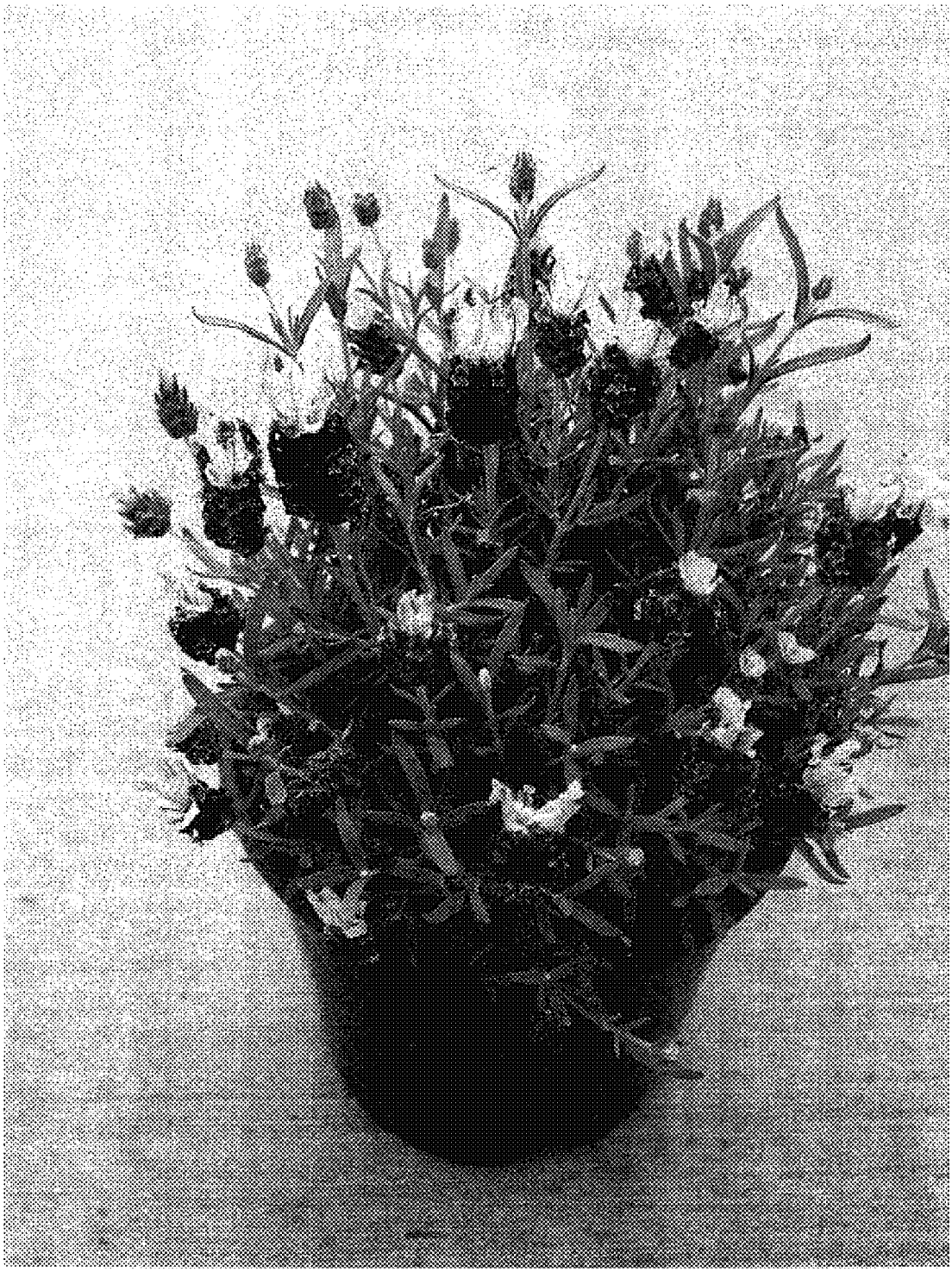
FIG. 1 depicts the plant in bloom from a side perspective.
Figure 2:
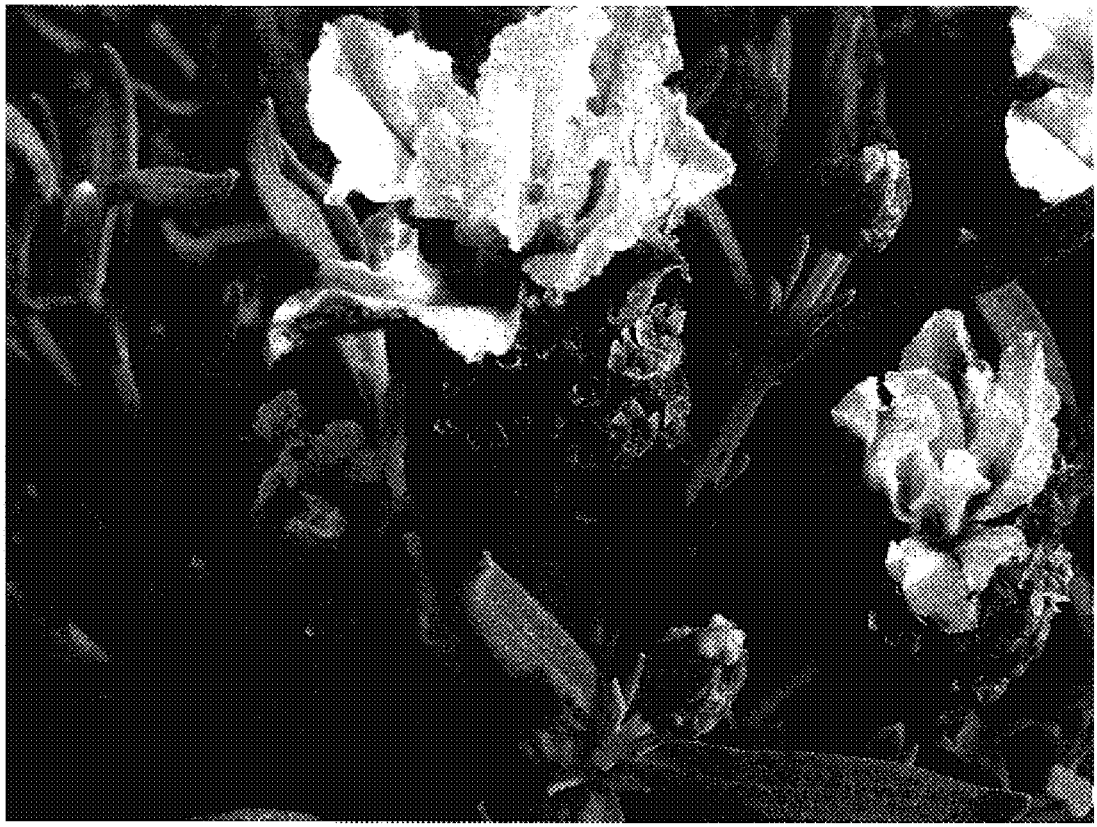
FIG. 2 depicts a close-up view of the flower spike. Drawings were made using conventional techniques and although the leaf and flower colors may appear different from the actual colors due to light reflectance, they are as accurate as possible by conventional photography.

The following is a detailed botanical description of the *Lavandula* cultivar named 'BOYSENBERRY RUFFLES'. Data was collected in Arroyo Grande, Calif. from 9-month-old plants greenhouse grown in 16 cm. containers. Color determinations are made in accordance with the 2001 Royal Horticultural Society Colour Chart of London, England, except where general color terms of ordinary dictionary significance are used. The growing requirements are similar to the species.

Classification:

*Botanical classification.*—*Lavandula stoechas* 'BOYSENBERRY RUFFLES'.
*Family.*—Lamiaceae.
*Genus.*—Lavandula.
*Species.*—*Stoechas.*
*Variety denomination.*—'BOYSENBERRY RUFFLES'.
*Common name.*—Lavender.

Plant:

*Habit.*—Dense.
*Height* (*at maturity*).—60 cm.
*Width* (*at maturity*).—70 cm.
*Life cycle.*—Perennial.
*Use.*—Ornamental for container or landscape.
*Vigour.*—Moderate.
*Hardiness.*—USDA Zone 8.
*Propagation.*—tip and stem cuttings.
*Root system.*—Fibrous.
*Cultural requirements.*—Full sun, adequate but not excess water, and well-draining soil.
*Time to produce a rooted cutting.*—4–6 weeks.
*Time to produce a* 10 cm. container plant in bloom.—20 weeks.
*Seasonal interest.*—Flower spikes in spring and summer.
*Parentage.*—*Lavandula stoechas* 'BOYSENBERRY RUFFLES' IS A selection that resulted from controlled cross-pollination of the following parents: Female parent plant: *Lavandula stoechas* 'Kew Red'. Male parent plant: *Lavandula stoechas* 'Pukehou'.
*Disease and insect resistance.*—Minimal disease and insect susceptibility with occasional aphids on new growth.

Stem:

*Branching.*—Erect.
*Stem shape.*—Quadrangular.
*Stem surface.*—Pubescent.
*Pubescence color.*—156D.
*Stem color.*—191B.
*Stem length.*—Average is 7 cm.
*Stem width.*—3 mm.
*Stem fragrance.*—Resinous scent.
*Internode length.*—Average is 1.25 cm.

Foliage:

*Leaf arrangement.*—Opposite.
*Leaf division.*—Simple.
*Leaf shape.*—Linear.
*Leaf margin.*—Entire.
*Leaf apex.*—Acute.
*Leaf base.*—Truncate.
*Leaf attachment.*—Sessile.
*Leaf color* (*adaxial surface*).—189A.
*Leaf color* (*abaxial surface*).—191A.
*Leaf surface* (*adaxial and abaxial surfaces*).—Tomentose.
*Tomenta color.*—156D.
*Venation.*—Prominent mid-vein observed.
*Vein color* (*adaxial surface*).—189A.
*Vein color* (*abaxial surface*).—191A.
*Leaf length.*—Average is 2.75 cm.
*Leaf width.*—Average is 0.40 cm.
*Leaf fragrance.*—Resinous scent.

Inflorescence:

*Fragrance.*—Resinous scent.
*Blooming period.*—April through August.
*Inflorescence type.*—Spike.
*Spike length.*—3.50 cm.
*Spike diameter.*—1.50 cm.
*Spike shape.*—Ovoid.
*Spike quantity.*—27–35.
*Peduncle length.*—2.50 cm.
*Peduncle width.*—3 mm.
*Peduncle shape.*—Quadrangular.
*Peduncle color.*—191C.
*Peduncle surface.*—Tomentose.
*Tomenta color.*—156D.

*Bud dimensions.*—3 mm in length and 1.50 mm in width.
*Bud shape.*—Ovoid.
*Bud color.*—138A.
*Bud surface.*—Lanate.
*Bud apex.*—Acute. (individual flower is referred to as corolla)
*Corolla number.*—Range of 20–30 on an individual spike.
*Corolla color.*—N72A fading to N79D.
*Corolla shape.*—Salverform.
*Corolla depth.*—8 mm.
*Corolla diameter.*—3 mm.
*Corolla tube depth.*—7 mm.
*Corolla tube diameter.*—2.50 mm.
*Petals.*—Four in number.
*Petals fused or unfused.*—Basally fused.
*Petal shape.*—Reniform.
*Petal length.*—1 mm.
*Petal width.*—1.25 mm.
*Petal apex.*—Obtuse and emarginated petal apices individually observed on an individual corolla.
*Petal margin.*—Entire.
*Petal surfaces* (*adaxial and abaxial*).—Glabrous.
*Petal color* (*adaxial and abaxial surfaces*).—N72A fading to N79D.
*Calyx color.*—138B.
*Calyx shape.*—Tubular.
*Calyx surface.*—Lanate.
*Color of hairs.*—155B.
*Calyx length.*—6 mm.
*Calyx width.*—3 mm.
*Sepals.*—Four in number.
*Sepals fused or unfused.*—Fused along three quarters of the length.
*Sepal apex.*—Acute. (Fertile bract)
*Fertile bract shape.*—Cordate.
*Quantity.*—Average of 20 per inflorescence.
*Fertile bract length.*—1 cm.
*Fertile bract width.*—0.50 cm.
*Fertile bract color* (*ventral and dorsal surfaces*).—Individual colors 138D and 138B are present on an individual fertile bract.
*Vein pattern.*—Reticulate.
*Vein color* (*ventral and dorsal surfaces*).—138B.
*Fertile bract apex.*—Acute.
*Fertile bract base.*—Cordate.
*Fertile bract surfaces* (*ventral and dorsal*).—Lanate.
*Fertile bract margin.*—Entire. (Sterile bract)
*Sterile bracts.*—Average of 5 per spike.
*Arrangement.*—Whorled.
*Sterile bract appearance.*—Irridescent.
*Sterile bract form.*—Petaloid.
*Sterile bract surfaces* (*abaxial and adaxial*).—Pubsecent.
*Color of hairs.*—155B.
*Sterile bract shape.*—Oblong-obovate.
*Sterile bract margin.*—Combination of sinuous and entire.
*Sterile bract length.*—Range of 0.75 cm. to 2 cm.
*Sterile bract width.*—Range of 0.40 cm. to 0.75 cm.
*Sterile bract apex.*—Obtuse.
*Sterile bract base.*—Rounded.
*Sterile bract color* (*abaxial and adaxial surfaces*).—75B and 75C.
*Vein pattern.*—Reticulate.
*Vein color* (*abaxial and adaxial surfaces*).—Individual 138B (green) veins and individual 79C or N77C (dark purple) veins.

Reproductive organs:
*Stamens.*—Four in number.
*Stamen form.*—Adnate to ventral surface of corolla tube.
*Stamen color.*—155C.
*Stamen length.*—5 mm.
*Anther.*—Four.
*Anther color.*—161A.
*Pollen color.*—161C.
*Pollen quantity.*—Moderate.
*Pistil.*—One.
*Pistil length.*—3 mm.
*Pistil color.*—155B.
*Stigma height.*—Less than 0.50 mm.
*Stigma surface.*—Glossy.
*Stigma shape.*—Orbicular.
*Stigma color.*—79A.
*Ovary dimensions.*—Less than 0.50 mm.
*Ovary shape.*—Globose.
*Ovary color.*—138A.
*Ovary position.*—Superior.

Seed: No seed has been observed to date.

It is claimed:

1. A new and distinct variety of *Lavandula* plant named 'BOYSENBERRY RUFFLES' as described and illustrated herein.

* * * * *